(12) United States Patent
Jakkula et al.

(10) Patent No.: US 7,982,469 B2
(45) Date of Patent: Jul. 19, 2011

(54) METHOD AND MEASURING DEVICE FOR RADIO WAVE MEASURING

(75) Inventors: Pekka Jakkula, Oulu (FI); Mikko Vuolteenaho, Kiiminki (FI); Mika Väisänen, Uusikaupunki (FI)

(73) Assignee: Senfit Oy, Oulu (FI)

( * ) Notice: Subject to any disclaimer, the term of this patent is extended or adjusted under 35 U.S.C. 154(b) by 419 days.

(21) Appl. No.: 12/305,291

(22) PCT Filed: Jun. 14, 2007

(86) PCT No.: PCT/FI2007/050355
§ 371 (c)(1),
(2), (4) Date: Dec. 17, 2008

(87) PCT Pub. No.: WO2007/147937
PCT Pub. Date: Dec. 27, 2007

(65) Prior Publication Data
US 2009/0278552 A1    Nov. 12, 2009

(30) Foreign Application Priority Data
Jun. 22, 2006 (FI) .................................... 20065439

(51) Int. Cl.
*G01R 27/04* (2006.01)
(52) U.S. Cl. ................... 324/633; 324/637; 324/644
(58) Field of Classification Search .................. 324/633, 324/637–644
See application file for complete search history.

(56) References Cited

U.S. PATENT DOCUMENTS

| | | | |
|---|---|---|---|
| 3,458,808 A | 7/1969 | Agdur | |
| 3,522,527 A | 8/1970 | Williams et al. | |
| 4,623,835 A | 11/1986 | Mehdizadeh et al. | |
| 4,890,054 A | 12/1989 | Maeno et al. | |
| 5,397,993 A | 3/1995 | Tews et al. | |
| 5,770,977 A | 6/1998 | Uurtamo | |
| 6,107,809 A * | 8/2000 | Moshe et al. ................. | 324/640 |
| 6,147,503 A * | 11/2000 | Nelson et al. ................. | 324/637 |
| 6,496,018 B1 | 12/2002 | Nagata et al. | |
| 7,330,034 B1 * | 2/2008 | Pelletier et al. ............... | 324/640 |

FOREIGN PATENT DOCUMENTS

| | | |
|---|---|---|
| EP | 1624298 A2 | 2/2006 |
| FI | 20055326 | 12/2006 |
| GB | 1118096 | 6/1968 |
| WO | 2006032730 A1 | 3/2006 |
| WO | 2006134237 A1 | 12/2006 |

* cited by examiner

*Primary Examiner* — Vincent Q Nguyen
(74) *Attorney, Agent, or Firm* — Hoffmann & Baron, LLP

(57) ABSTRACT

A generator generates radio-frequency electromagnetic radiation to a resonator whose resonance frequency is affected by a characteristic to be measured of an object to be measured. A receiver receives radio-frequency electromagnetic radiation from the resonator and a signal processing unit searches for a resonance frequency of the resonator for measuring the characteristic to be measured. The generator comprises a digital frequency synthesizer for scanning a frequency of radio-frequency electromagnetic radiation to be applied to the resonator over a desired frequency band by using discrete measuring frequencies.

14 Claims, 7 Drawing Sheets

METHOD AND MEASURING DEVICE FOR RADIO WAVE MEASURING

CROSS-REFERENCE TO RELATED APPLICATIONS

This application is a National Phase application of International Application No. PCT/FI2007/050355 filed Jun. 14, 2007, which claims priority based on Finnish Application No. 20065439 filed Jun. 22, 2006, which are incorporated herein by reference.

BACKGROUND

1. Field

The invention relates to a method and a measuring device for measuring an object by radio-frequency electromagnetic radiation.

2. Description of the Related Art

Measuring by radio and microwave frequencies may employ as a sensor a resonator that is designed such that characteristics of the object to be measured affect the resonance frequency of the resonator. Because, in general, only one characteristic is measured, the objective is, that at least approximately, the object to be measured has only one factor that affects the resonance frequency. When the frequency of electromagnetic radiation to be applied to the resonator is scanned over a frequency band used for measuring, a resonance frequency may be searched for in the response signal received from the resonator. In order to be able to determine the desired characteristic of an object to be measured by means of the resonance frequency, prior to actual measuring it is necessary to carry out calibration measurements, in which objects to be measured have predetermined characteristics. In this manner it is possible to set correlation between various resonance frequency values and values of characteristics to be measured.

In prior art the measuring is performed such that a band to be measured is scanned over by a VCO (Voltage Controlled Oscillator) or a YIG (Yttrium-Iron Garnet) oscillator. The resonator output is detected, amplified and converted from analog to digital. From a digital signal it is possible to determine medium frequency, half-power width, Q-value and/or signal level of the resonator.

Measuring involves several problems, however. Measuring is most accurate immediately after calibration, but measuring error increases the higher the more time passes or the more measurements there are performed after calibration. The error may be reduced by performing more frequent calibrations, but this, in turn, decreases, slows down or even disturbs the actual measurement use. The band to be measured, which is scanned over, by the VCO and the YIG oscillator, is excessively narrow for many measurements. In addition, scanning over the band to be measured takes place too slowly in view of many applications.

SUMMARY

The object of the invention is to provide an improved method and a measuring device implementing the method. This is achieved by a method for measuring an object to be measured by means of radio-frequency electromagnetic radiation, which is comprised by applying radio-frequency electromagnetic radiation to at least one resonator, the resonance frequency of which is affected by a measured characteristic of the object to be measured; receiving radio-frequency electromagnetic radiation from the at least one resonator; and searching the received frequency band for a resonance frequency of the at least one resonator in order for measuring a characteristic to be measured. The method further scans the radio-frequency electromagnetic radiation frequency applied to the at least one resonator over a desired frequency band by using discrete measuring frequencies, the forming of which utilizes digital synthesis.

The object of the invention is also to provide a measuring device for measuring an object to be measured by means of radio-frequency electromagnetic radiation, the measuring device comprising a generator for generating radio-frequency electromagnetic radiation; at least one resonator that is configured to receive radiation generated by the generator and the resonance frequency of which is affected by a measured characteristic of the object to be measured; a receiver that is configured to receive radio-frequency electromagnetic radiation from the at least one resonator; and a signal processing unit that is configured to search the received frequency band for a resonance frequency of the at least one resonator in order for measuring a characteristic to be measured. The generator comprises a digital frequency synthesizer for scanning a frequency of radio-frequency electromagnetic radiation applied to the at least one resonator over a desired frequency band by using discrete measuring frequencies.

Preferred embodiments of the invention are disclosed in the dependent claims.

Several advantages are achieved by the method and the system in accordance with the invention. The accuracy of measuring remains almost unchanged in view of measuring frequency and time, resulting from the fact that in the solution signal generation is based on an accurate temperature stable crystal. Therefore there is little need for external calibration. A measuring band may be wide, if need be. In addition, a scan over a band to be measured may be carried out quickly. The measuring concept may be used in applications, where propagation time, phase, attenuation or the like will be measured.

BRIEF DESCRIPTION OF THE DRAWINGS

In the following the invention will be described in connection with preferred embodiments, with reference to the attached drawings, in which.

DETAILED DESCRIPTION

Figure 1:
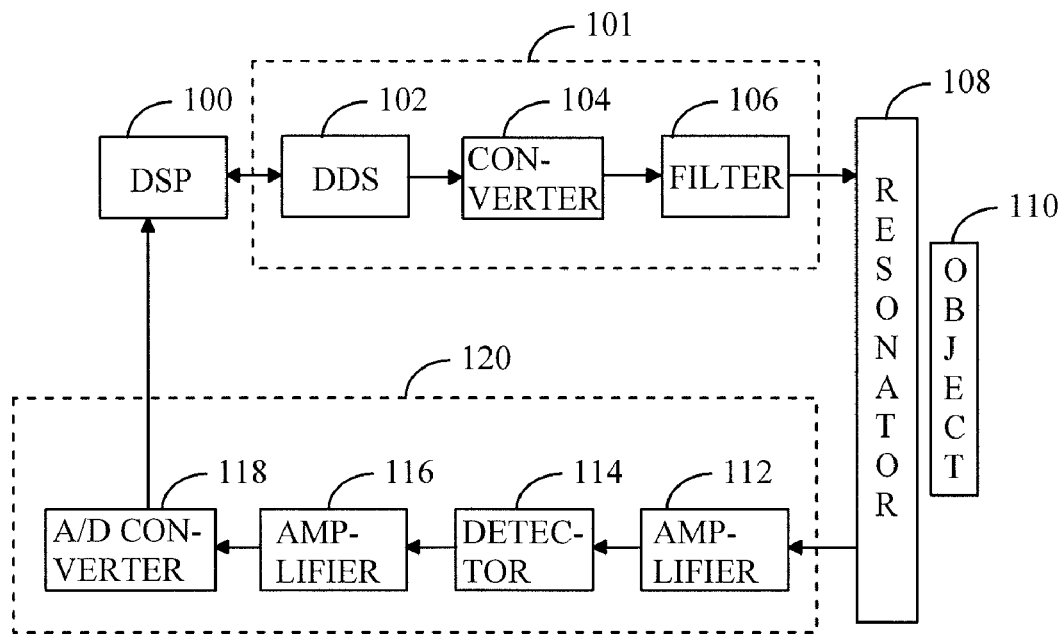
FIG. 1 shows a measuring device.

FIG. 1 shows a measuring device which may comprise a digital signal processing unit 100, a generator 101 generating radio-frequency electromagnetic radiation, a resonator 108 and a receiver 120. The generator 101 may comprise a digital frequency synthesizer 102, a frequency converter 104 and a filter 106. The receiver 120, in turn, may comprise a preamplifier 112, a detector 114, an amplifier 116 and an A/D converter 118, which converts an analog signal to a digital signal.

The digital signal processing unit 100 may be a computer, such as a PC (Personal Computer) or a signal processor, which comprises a processor, memory and computer software suitable for signal processing. The digital signal processing unit 100 may control at least one parameter in the digital frequency synthesizer 102, which may operate on DDS (Direct Digital Synthesis) principle.

The frequency synthesizer operating on DDS principle comprises a memory, which stores digital sample values of waveforms associated with frequencies to be synthesized. When a waveform is synthesized to an output signal of the frequency synthesizer 102 the sample values of a desired waveform are retrieved from the memory and a waveform corresponding thereto is generated in the same manner as when forming a sine wave by means of a look-up table. When scanning is performed over a predetermined frequency band, the waveform is altered such that the output frequency of the frequency synthesizer 102 shifts from a discrete frequency to a next discrete frequency.

In the digital frequency synthesizer 102 at least one parameter to be controlled may be one of the following: band of the frequency synthesizer, value of each discrete frequency of the frequency synthesizer, the number of frequencies on the band, resolution of the frequencies, the generating order of the frequencies. The band may be 0 to 400 MHz, for instance, but the band may also be narrower or wider and it may also start from a frequency other than 0 Hz. The discrete frequencies may be determined, for instance, to be at even intervals, and the interval may be e.g. 10 Hz, which also corresponds to the resolution of the frequencies. The frequencies may be determined, for instance, iteratively in the following manner: $f_{k+1}=f_k+\Delta f$, where f is frequency, k is index of frequency f and $\Delta f$ is frequency interval. If band B is 400 MHz and the frequency interval is 10 Hz, there are obtained $B/\Delta t$ frequencies, i.e. in this example 40 000 000 discrete spot frequencies to be used in measuring. Discrete frequencies need not be generated at even intervals, but the interval between frequencies may change as a function of time, for instance such that the difference between two successive frequencies $\Delta f=f_{k+1}-f_k$ is smaller on low frequencies than on high frequencies. Other frequency differences are also possible. The frequencies may be generated in the digital frequency synthesizer 102 in an order from lowest to highest or highest to lowest. The frequencies may also be generated according to a predetermined function or in random order. The frequencies remain unchanged with great accuracy in view of the number of measurings and time because in the solution signal generation is based on an accurate temperature stable crystal.

Frequencies generated by the digital frequency synthesizer 102 may be used directly in the measuring, but the frequencies generated by the digital frequency synthesizer 102 may also be pre-frequencies, which are shifted from the predetermined frequency band produced by the frequency synthesizer 102 to be discrete measuring frequencies of a desired frequency band by means of a frequency converter 104. The frequency converter 104 may be a mixer, a frequency multiplier or a matrix consisting thereof, whose operation may be controlled by a digital signal processing unit 100. The measuring frequencies to be applied to the resonator 108 may then be within the range of 0 Hz to 300 GHz.

Figure 2A:
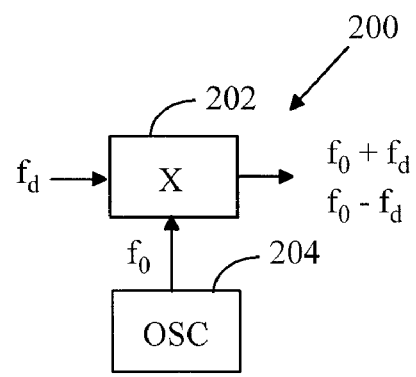
FIG. 2A shows a mixer.

FIG. 2A shows mixer coupling 200, in which a signal of frequency $f_o$ from the oscillator 204 and a signal from the digital frequency synthesizer 104, whose frequency may be represented by variable $f_d$, for the sake of simplicity, are applied to the mixer 202. The mixer 202 mixes the signals, and there are formed signals whose frequencies are $(f_o+f_d)$ and $(f_o-f_d)$. Of these signals the one at the difference frequency $(f_o-f_d)$ may be deleted with a filter 106, and consequently the measuring frequency band is the same as the frequency band generated by the digital frequency synthesizer 104, but it is at a higher frequency. In this manner it was possible to shift the whole frequency band generated by the digital frequency synthesizer 104 to the desired measuring band.

Figure 2B:
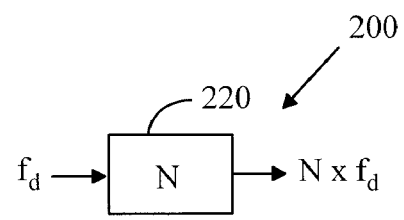
FIG. 2B shows a frequency multiplier.

FIG. 2B shows a frequency multiplier 220. The frequency multiplier is a non-linear component, which may be active or passive, and the output signal frequency of which is higher than the input signal frequency. The frequency multiplier may be implemented for instance such that an overcontrolled diode generates harmonic frequencies, whereof other than the desired frequency are filtered out. The frequency multiplier 220 multiplies the frequency of the signal fed therein by factor N, which may be a real number, for instance, a positive integer.

Let us study again FIG. 1. When radio-frequency electromagnetic radiation is applied to a resonator 108, an object to be measured 110 affects the resonance frequency of the resonator 108. The radio-frequency electromagnetic radiation from the resonator 108 is received and may be amplified in a preamplifier 112. The preamplifier 112 is not necessarily needed, however. Thereafter, the amplified signal propagates to a detector 114, and the direct voltage value at the output thereof depends on the strength of the received signal. The direct voltage may be further amplified in an amplifier 116, which is not necessarily needed, however. Eventually, the analog signal propagating in the reception chain will be converted to a digital signal in a converter 118 and it is applied to a digital signal processing unit 100, where a resonance frequency will be searched. On the basis of the found resonance frequency it is possible to measure a characteristic of the object to be measured 110.

Figure 3:
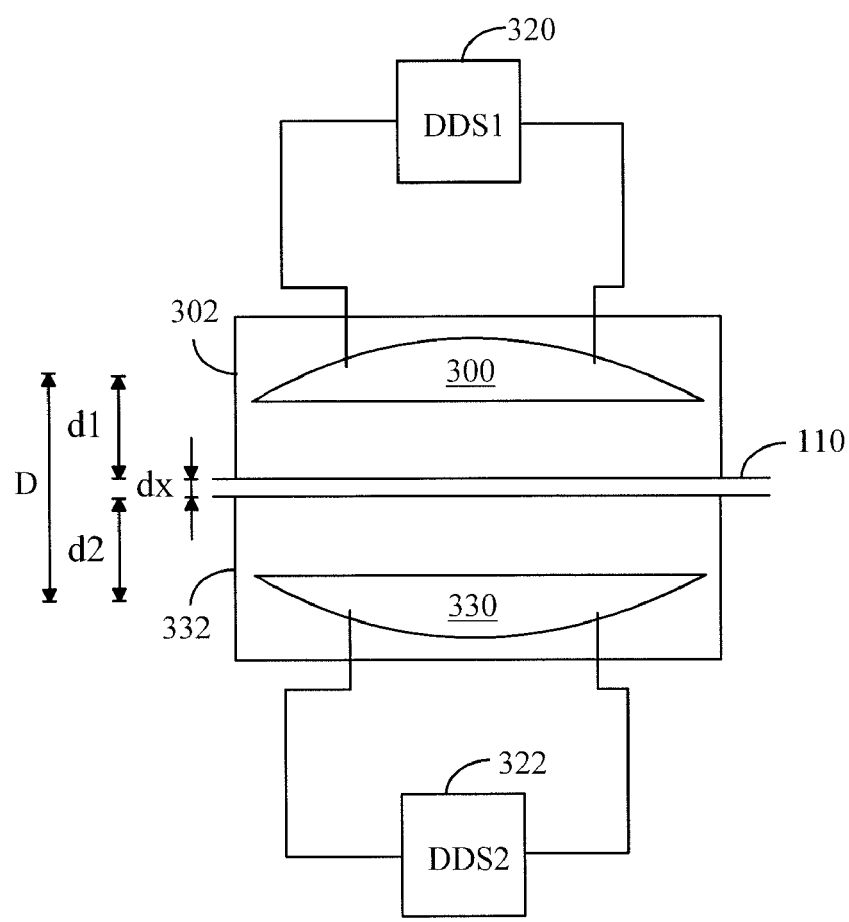
FIG. 3 shows a measuring arrangement for plate thickness.

FIG. 3 shows the principle of the solution to measure the thickness dx of a plate. This solution uses two open resonators which are directed towards one another and between which the plate to be measured is intended to be at the moment of measuring. In order for the plate to reflect the radio-frequency radiation directed thereto, the plate is to be well conductive, such as a metal plate. Two resonators directed towards one another form a resonator pair. When the object to be measured 110 is brought between the resonator mirrors 300, 330 directed towards one another, there are formed two resonators 302, 332. Each one of the resonators 302, 332 may have a specific generator 320, 322. The resonance frequency of the resonator 302 is determined by a distance d1 between the resonator mirror 300 and the upper surface 312 of the object to be measured 110. Correspondingly, the resonance frequency of the resonator 332 is determined by a distance d2 between the resonator mirror 330 and the lower surface of the object to be measured 110. As the distance between the resonator mirrors 300, 302 is known, the thickness dx of the plate may be defined, for instance, as follows: dx=D−(d1+d2). This measuring has an advantage, for instance, that measuring on different sides of the plate is (nearly) simultaneous, whereby vibration of the plate and/or some other motion does not disturb the measuring.

Figure 4A:
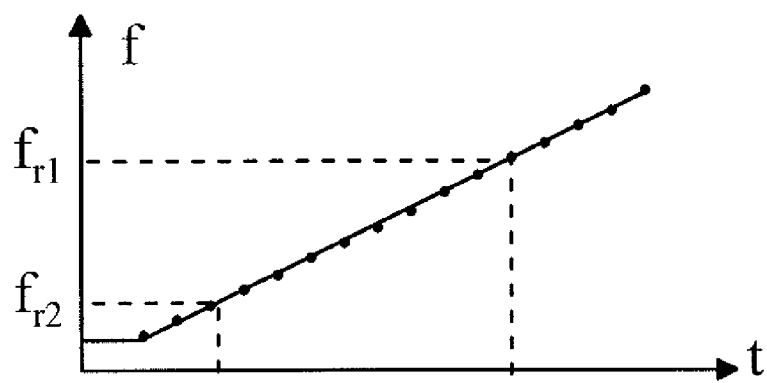
FIG. 4A shows a measuring frequency scan from a low frequency to a high frequency.
Figure 4B:
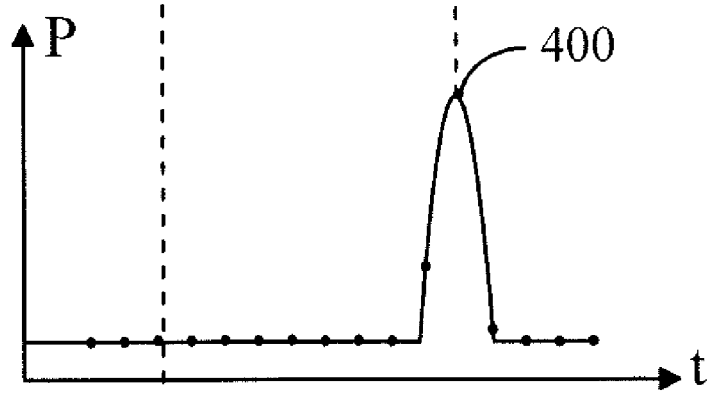
FIG. 4B shows strength of a measured signal as a function of time measured from above the object to be measured.
Figure 4C:
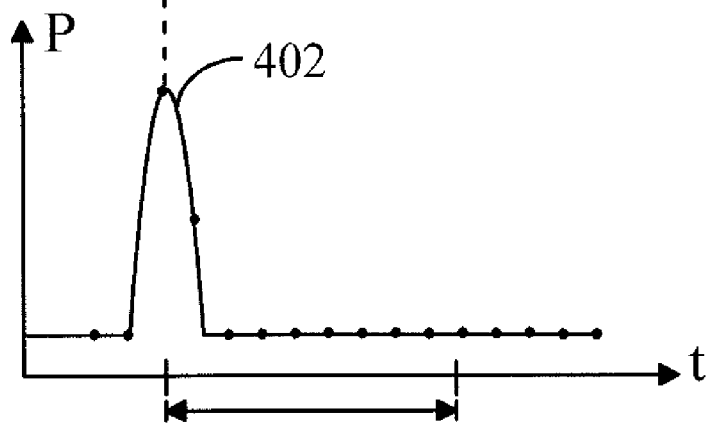
FIG. 4C shows strength of a measured signal as a function of time measured from below the object to be measured.
Figure 4D:
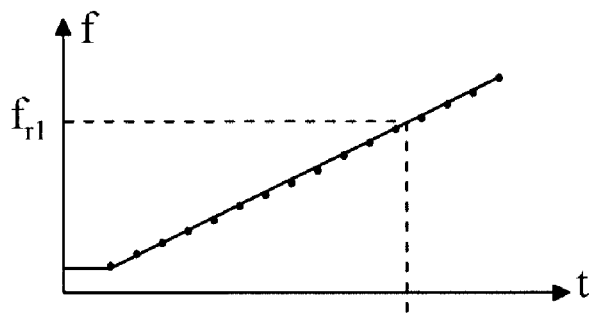
FIG. 4D shows a measuring frequency scan from a low frequency to a high frequency.
Figure 4E:
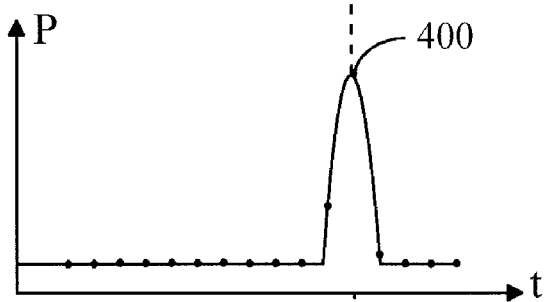
FIG. 4E shows strength of a measured signal as a function of time measured from above the object to be measured.
Figure 4F:
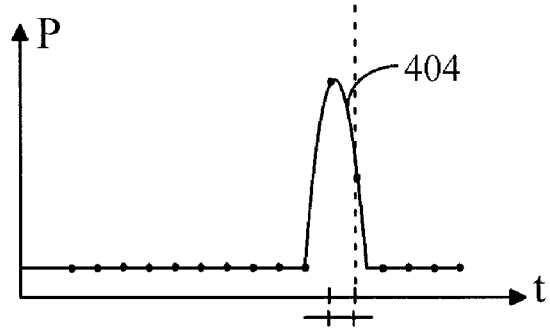
FIG. 4F shows strength of a measured signal as a function of time measured from below the object to be measured.
Figure 4G:
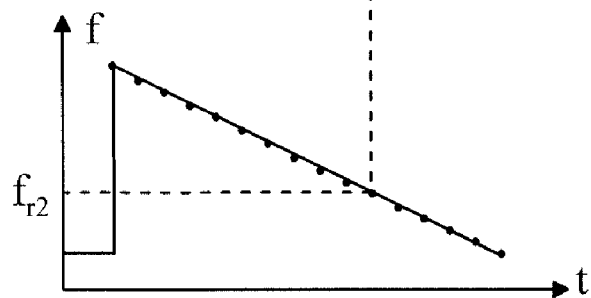
FIG. 4G shows a measuring frequency scan from a high frequency to a low frequency.

FIGS. 4A to 4G show how the order of measuring frequencies affects the measuring moment when the measuring arrangement of FIG. 3 is used. In FIGS. 4A, 4D and 4G the vertical axis represents frequency f and the horizontal axis represents time t. In FIGS. 4B, 4C, 4E and 4F the vertical axis represents strength P of the measuring signal and the horizontal axis represents time t. FIG. 4A shows a situation, in which both a frequency scan of the resonator 302 above the object to be measured and a frequency scan of the resonator 332 beneath the object to be measured are performed in the same direction. Scanning over a measuring band may start at time instant to from the lowest frequency $f_1$ and ends at time instant $t_1$ to the highest frequency $f_h$.

If we assume that the surface of the object to be measured 110 is closer to the resonator 302 above the object to be measured 110 than the resonator 332 beneath the object to be measured 110, the resonance frequency is higher in the resonator 302 above the object to be measured 110 than in the resonator 332 beneath the object to be measured 110. FIG. 4B shows a resonance spike 400 of the resonator 302 above the object to be measured 110. FIG. 4C shows a resonance spike 402 of the resonator 332 beneath the object to be measured 110. FIGS. 4B and 4C are mutually arranged such that the difference Δt in finding times between the resonance frequencies 400, 402 may be detected. The difference Δt may be determined by means of a scanning velocity $v_p$ and the difference in resonance frequencies $\Delta f=f_{r1}-f_{r2}$, $\Delta t=\Delta f/v_p$, and the difference Δt depends on the thickness of the plate to be measured.

FIG. 4D is the same as FIG. 4A. FIG. 4G shows a situation, in which a frequency scan of the resonator beneath the object to be measured 110 is performed from the highest frequency of the band to the lowest frequency of the band. FIG. 4E is the same as FIG. 4B. FIG. 4F shows the resonance frequency 404 of the resonator 332 beneath the object to be measured 110. Because scans were performed in different directions, the difference Δt in measuring time instants is much smaller than in a case where scanning was performed in the same direction. This difference appears from the figures, because the time axes in FIGS. 4D to 4G have been mutually arranged.

Figure 5:
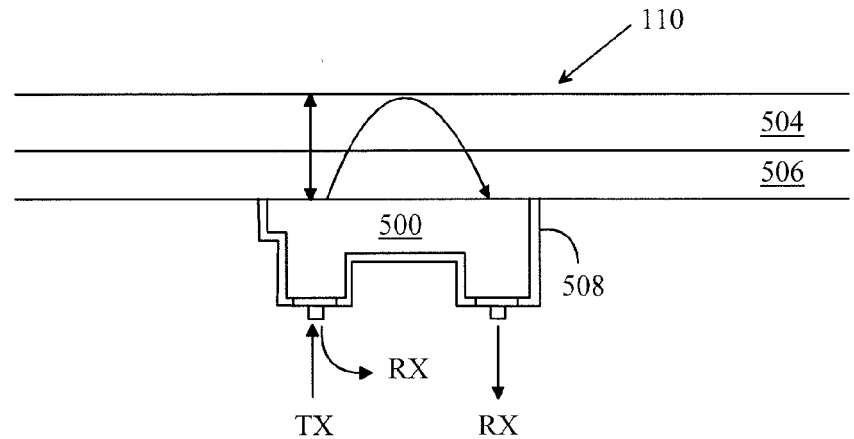
FIG. 5 shows a dewatering element as a resonator.

Instead of or in addition to measuring a plate thickness, the presented solution also allows measuring water content in a web (and a wire) when making paper, board or cardboard. Measuring may be performed, for instance, in the wire section of the paper machine by means of a dewatering element shown in FIG. 5. Water content measuring is not restricted to this exemplary application, however. In general, it is possible to measure any material whose permittivity changes as a function of any parameter.

The dewatering element 500 is in contact with the object to be measured 110, which include at least the web 504 and the wire 506. It is possible that on the web 504 there is still another wire. The web 504 may be water-containing wood pulp used for paper or board making. In the former section of the paper machine water is removed from the web 504, and therefore measuring the amount of water in machine direction or in a direction trans-verse to machine direction is useful. The dewatering element 500 may be coated with metal or other conductive material 508 on surfaces other than the one that is in contact with the object to be measured 110. The structure of the dewatering element 500 may otherwise be of ceramic with permittivity higher than 75 at the frequency used for measuring. Permittivity may be, for instance, 80 to 100. The near field formed by the dewatering element 500 may extend to the object to be measured 110 as indicated by the arrows.

Figure 6:
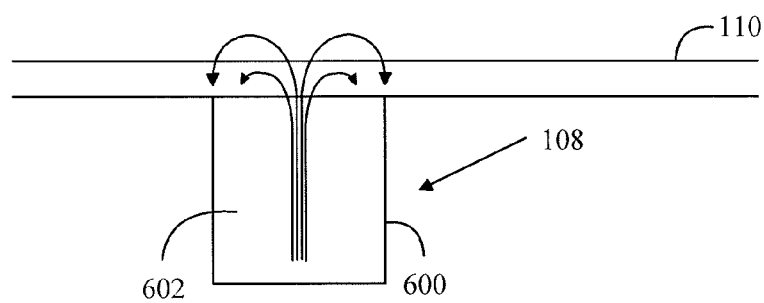
FIG. 6 shows a waveguide cavity.

FIG. 6 shows a solution, in which the resonator 108 may operate like a waveguide. The exterior 600 of the resonator 106, which is able to produce a short-circuit in the lower part, may be of metal or some other conductive material, and inside the exterior there may be, for instance, ceramic 602. Field lines of an electric near field may be drawn to start from the centre of the resonator 108 and to curve towards the exterior 600 of the object to be measured 110. Thus the water in the object to be measured is able to affect the resonance frequency to be generated. The resonator 108 may operate by a non-radiating waveform $TM_{01}$ or by waveform $TM_{11}$.

Figure 7:
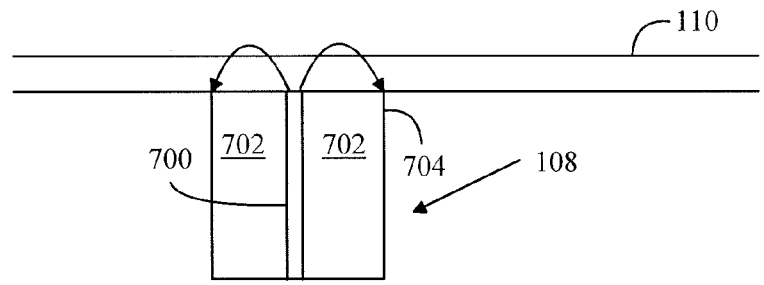
FIG. 7 shows a coaxial resonator.

FIG. 7 shows a solution, in which the resonator 108 operates like a coaxial resonator. In this solution there is metal or other conductive material 700 in the centre of the resonator 108. Around the conductive centre part 700 there may be ceramic 702. The outer circumference 704 of the coaxial resonator is, in turn, of conductive material in the same way as the centre part 700. Also in this solution the field lines of the electric near field start from the centre of the resonator 108 and curve through the object to be measured 110 towards the edges. Thus the water in the object to be measured is able to affect the resonance frequency to be generated.

Figure 8:
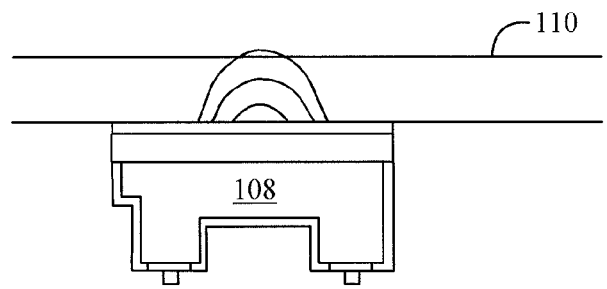
FIG. 8 shows a slot resonator field in an object to be measured.

The resonator 108 wherewith water content is measured may also comprise a radiating slot in a metal plate, which may be, for instance, plating of a circuit board. The curved slot may constitute a (near) circle, whereby its electric field radiated to a far field is (almost) completely cancelled. The centre line of the slot may form a curve that is linear in sections. The centre line of the slot may also form a curve with continuous curvature like in a non-linear function with continuous derivative. The centre line of the slot may also represent a non-self-crossing arched curve. FIG. 8 shows near field lines of a near field that start from the slot and extend up to the object to be measured 110. Thus the water in the object to be measured is able to affect the resonance frequency to be generated.

Figure 9:
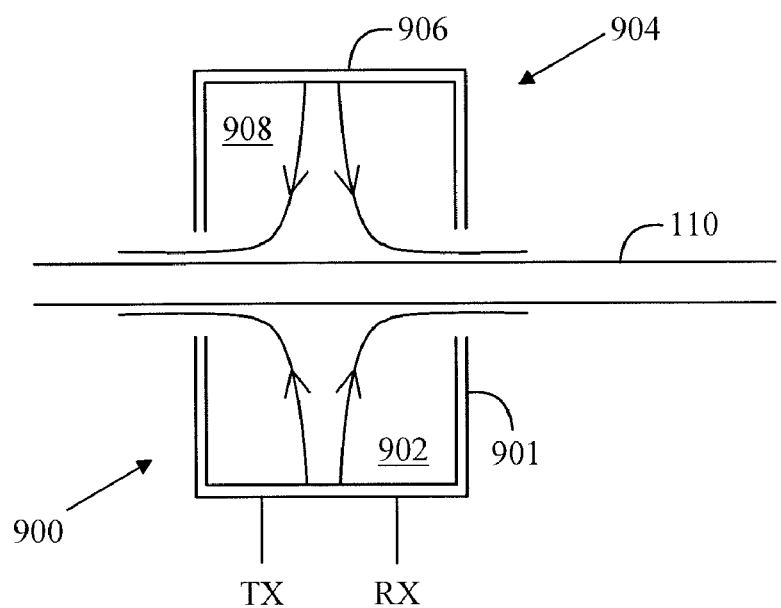
FIG. 9 shows a waveguide cavity consisting of an active part and a passive part.

FIG. 9 shows a waveguide cavity for measuring water content, for instance. The actual active resonator part 900, which is on one side of the object to be measured 110, comprises on its outer surface 901 metal that extends everywhere else but to the surface that is directed to the object to be measured 110 or comes into contact with the object to be measured 110. The interior 902 of the active resonator part 900 may be of isolating material, such as Teflon or ceramic. The active resonator part 900 also comprises an input contact TX and an output contact RX of radio-frequency electromagnetic radiation. On the other side of the object to be measured 110 there may be a passive part 904 of the resonator 108, whose outer surface 906 is of metal and the interior 908 of isolating material, such as Teflon or ceramic. Radiation is not applied to nor received from the passive part 904. The active part and the passive part of the resonator may have the same shape and they may be mutually directed as if they were mirror images of one another. A resonator of this kind does not radiate to a far field, and consequently it does not interfere with other measurings or other devices. In FIG. 9 there are also drawn field lines and they are symmetrical to the active resonator part 900 and the passive resonator part 904. Because permittivity inside both the active resonator part 900 and the passive resonator part 904 is higher than in the ambient air in the object to be measured 110, the power of the electromagnetic field is (relatively) even in the object to be measured 110. Moisture in the object to be measured 110 may also be measured without the passive part 904. In that case the resonator only includes the active resonator part 900.

Figure 10:
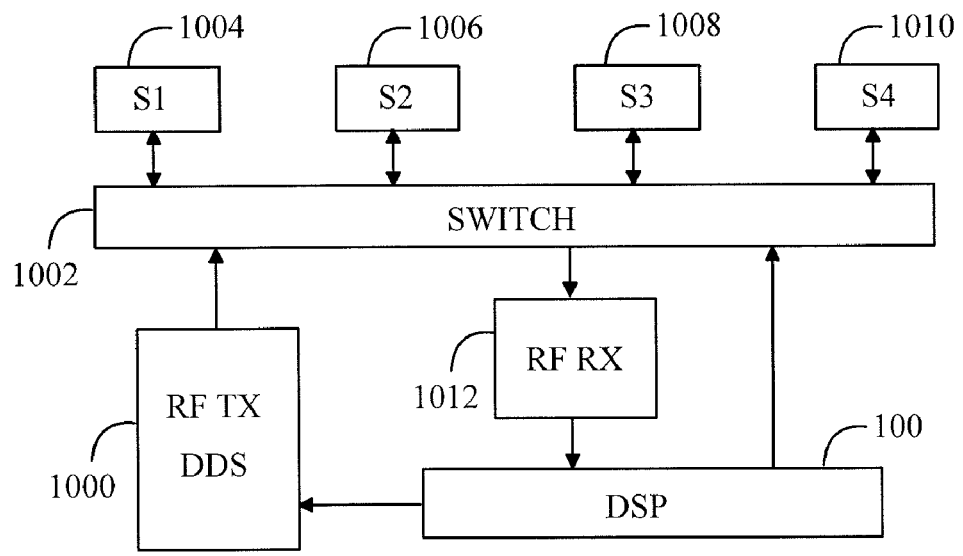
FIG. 10 shows measuring by a plurality of resonators.

FIG. 10 shows a solution which employs a plurality of resonators as sensors. The digital signal processing unit 100 controls a measuring frequency generator 1000 that generates measuring frequencies of radiation by means of a digital frequency synthesizer. The measuring frequency generator 1000 may comprise blocks 102 to 106 of FIG. 1. The radiation used in measuring is switched to resonators 1004 to 1010 with a switching unit 1002. When radiation is received from the resonators 1004 to 1010, the switching unit 1002 switches radiation from each resonator 1004 to 1010 to a receiver unit 1012 that may comprise blocks 112 to 118 of FIG. 1. The receiver unit 1012 forwards the measuring signal to the digital signal processing unit 100 for measuring operations. The digital signal processing unit 100 may control the operation of the switching unit 1002.

In the measurement of FIG. 10 it is possible to use N resonators 1004 to 1010, of which radio-frequency electromagnetic radiation is supplied to M resonators simultaneously. Then, N is a positive integer larger than one and M is a positive integer smaller than N. According to this example, radio-frequency electromagnetic radiation may be supplied to the resonators 1004 to 1010 such that between each two successive resonators receiving electromagnetic radiation there is at least one resonator that does not receive electromagnetic radiation. If the resonators are in line transversely to machine direction and they measure, for instance, water content of the web, the measuring may be performed with every fourth resonator at a time. When measuring is performed first with the first ones of every fourth resonator, the next measuring may be performed with the second ones of every fourth resonator. If this is carried on, the measurement results of all resonators will be obtained after four measurings.

Figure 11:
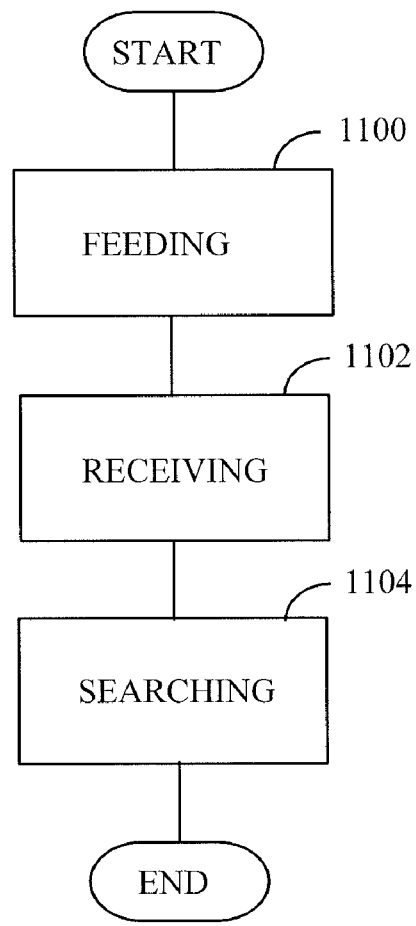
FIG. 11 is a flowchart of the method.

FIG. 11 is a flowchart of the method. In step 1100, radio-frequency electromagnetic radiation is applied to at least one resonator whose resonance frequency is affected by a characteristic of the object to be measured. In step 1102, radio-frequency electromagnetic radiation is received from at least one resonator. In step 1104, the received frequency band is searched for a resonance frequency of at least one resonator for measuring the characteristic to be measured.

Figure 12:
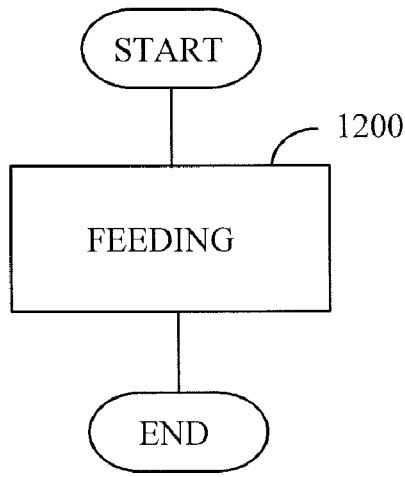
FIG. 12 is a flowchart associated with scanning.

FIG. 12 shows a method step to be performed in step 1100 of FIG. 11. In step 1200, the frequency of the electromagnetic radiation applied to at least one resonator is scanned over a desired frequency band by using discrete measuring frequencies, in the generation of which digital synthesis is utilized.

Even though the invention is described above with reference to the example in the attached drawings, it is apparent that the invention is not restricted thereto, but it may be modified in a variety of ways within the scope of the accompanying claims.

What is claimed is:

1. A method for measuring an object to be measured by means of radio-frequency electromagnetic radiation, comprising:
   applying radio-frequency electromagnetic radiation to at least one resonator, the resonance frequency of which is affected by a measured characteristic of the object to be measured;
   receiving radio-frequency electromagnetic radiation from the at least one resonator;
   searching the received frequency band for a resonance frequency of the at least one resonator in order for measuring a characteristic to be measured;
   applying radio-frequency electromagnetic radiation to at least two of the resonators which are directed towards one another and between which the object to be measured is to be placed;
   scanning the radio-frequency electromagnetic radiation frequencies applied to the at least two resonators over desired frequency bands by using discrete measuring frequencies, the forming of which utilizes digital synthesis; and
   controlling one resonator of at least two of the resonators such that scanning proceeds from low to high frequency; and controlling a second resonator of at least two of the resonators such that scanning proceeds from high to low frequency.

2. The method of claim 1, the method further comprising:
   generating discrete pre-frequencies for a predetermined frequency band with the direct digital synthesis; and
   shifting the discrete pre-frequencies from the predetermined frequency band to be discrete measuring frequencies of the desired frequency band by means of a frequency multiplier.

3. The method of claim 1, the method further comprising:
   generating discrete pre-frequencies for a predetermined frequency band with the direct digital synthesis; and
   shifting the discrete pre-frequencies from the predetermined frequency band to be discrete measuring frequencies of the desired frequency band by means of a mixer.

4. The method of claim 1, the method further comprising controlling the generation of the discrete measuring frequencies by determining at least of the following: value of each measuring frequency, the number of measuring frequencies on a desired frequency band, resolution of measuring frequencies, generation order of measuring frequencies.

5. The method of claim 1, the method further comprising;
   using in the measurement N resonators, where N is a positive integer larger than one; and
   applying radio-frequency electromagnetic radiation to M resonators at a time, where M is a positive integer smaller than N.

6. The method of claim 5, the method further comprising applying radio-frequency electromagnetic radiation to resonators such that between two successive resonators receiving electromagnetic radiation there is at least one resonator that does not receive electromagnetic radiation.

7. The method of claim 1, the method further comprising using in the measurement a waveguide cavity not radiating in the environment and comprising an active resonator part and a passive resonator part directed to one another, the object to be measured being intended for placement between the active resonator part and the passive resonator part.

8. A measuring device for measuring an object to be measured by means of radio-frequency electromagnetic radiation, the measuring device comprising:
   a generator for generating radio-frequency electromagnetic radiation;
   at least one resonator that is configured to receive radiation generated by the generator and whose resonance frequency is affected by a characteristic of the object to be measured;
   a receiver that is configured to receive radio-frequency electromagnetic radiation from the at least one resonator;
   a signal processing unit that is configured to search the received frequency band for a resonance frequency of at least one resonator for measuring a characteristic to be measured; and at least two such resonators which are directed towards one another and between which the object to be measured is to be placed, the generator comprising a digital frequency synthesizer for scanning a frequency of radio-frequency electromagnetic radiation applied to at least the two resonators over desired frequency bands by using discrete measuring frequencies, the digital signal processing unit being configured to control one resonator of at least the two resonators such that scanning proceeds from low frequency to high frequency and a second resonator of at least the two resonators such that scanning proceeds from high frequency to low frequency.

9. The measuring device of claim 8, wherein the digital frequency synthesizer is configured to generate with direct digital synthesis discrete pre-frequencies for a predetermined frequency band, the measuring device comprising a frequency converter which is a frequency multiplier and which is configured to shift the discrete pre-frequencies from the predetermined frequency band to be discrete measuring frequencies of the desired frequency band.

10. The measuring device of claim 8, wherein the digital frequency synthesizer is configured to generate with direct digital synthesis discrete pre-frequencies for a predetermined frequency band, the measuring device comprising a frequency converter which is a mixer and which is configured to shift the discrete pre-frequencies from the predetermined frequency band to be discrete measuring frequencies of the desired frequency band.

11. The measuring device of claim 8, wherein the measuring device comprises a digital signal processing unit which is configured to control the generation of discrete measuring frequencies by determining at least one of the following: value of each measuring frequency, the number of measuring frequencies on a desired frequency band, resolution of measuring frequencies, generating order of measuring frequencies.

12. The measuring device of claim 8, wherein the measuring device is configured to employ N resonators, where N is a positive integer larger than one, and radio-frequency electromagnetic radiation is applied to M resonators simultaneously, where M is a positive integer smaller than N.

13. The measuring device of claim 12, wherein the digital signal processing unit is configured to control application of radio-frequency electromagnetic radiation to the resonators such that at each moment between each two successive resonators receiving electromagnetic radiation there is at least one resonator that does not receive electromagnetic radiation.

14. The measuring device of claim 8, wherein the measuring device comprises at least one waveguide cavity which does not radiate to the environment and which comprises an active resonator part and a passive resonator part which are directed to one another, the object to be measured being intended for placement between the active resonator part and the passive resonator part.

* * * * *